US011564900B2

(12) United States Patent
Feuerstein

(10) Patent No.: US 11,564,900 B2
(45) Date of Patent: Jan. 31, 2023

(54) COMBINATION METHODS AND COMPOSITIONS INCLUDING SLEEP THERAPEUTICS FOR TREATING MOOD

(71) Applicant: Seth Feuerstein, Woodbridge, CT (US)

(72) Inventor: Seth Feuerstein, Woodbridge, CT (US)

(*) Notice: Subject to any disclaimer, the term of this patent is extended or adjusted under 35 U.S.C. 154(b) by 98 days.

(21) Appl. No.: 17/006,714

(22) Filed: Aug. 28, 2020

(65) Prior Publication Data
US 2021/0046035 A1 Feb. 18, 2021
US 2021/0361607 A9 Nov. 25, 2021

Related U.S. Application Data

(63) Continuation of application No. 15/909,923, filed on Mar. 1, 2018, now Pat. No. 10,758,508, which is a continuation of application No. 14/431,399, filed as application No. PCT/US2013/061588 on Sep. 25, 2013, now abandoned.

(60) Provisional application No. 61/705,669, filed on Sep. 26, 2012.

(51) Int. Cl.
*A61M 21/02* (2006.01)
*A61K 31/202* (2006.01)
*A61K 45/06* (2006.01)
*A61K 31/437* (2006.01)
*A61K 31/4985* (2006.01)
*A61M 21/00* (2006.01)
*A61K 36/35* (2006.01)

(52) U.S. Cl.
CPC .......... *A61K 31/202* (2013.01); *A61K 31/437* (2013.01); *A61K 31/4985* (2013.01); *A61K 36/35* (2013.01); *A61K 45/06* (2013.01); *A61M 21/00* (2013.01); *A61M 21/02* (2013.01)

(58) Field of Classification Search
CPC ......... A61M 21/00–02; A61B 5/16–18; A61B 5/4806–4818
See application file for complete search history.

(56) References Cited

U.S. PATENT DOCUMENTS

| 4,353,375 | A | 10/1982 | Colburn et al. |
| 10,758,508 | B2 | 9/2020 | Feuerstein |
| 2005/0113449 | A1 | 5/2005 | Renshaw |
| 2005/0176680 | A1 | 8/2005 | Lalji et al. |
| 2005/0245610 | A1 | 11/2005 | Verboom et al. |
| 2006/0160119 | A1 | 7/2006 | Turner et al. |
| 2006/0252761 | A1 | 11/2006 | Davis et al. |
| 2010/0041965 | A1* | 2/2010 | Kang ................ A61B 5/00 600/301 |
| 2010/0094103 | A1* | 4/2010 | Kaplan ............. A61M 21/00 600/26 |
| 2010/0130611 | A1 | 5/2010 | Feuerstein et al. |
| 2011/0003796 | A1 | 1/2011 | Reines et al. |
| 2011/0190594 | A1 | 8/2011 | Heit et al. |
| 2011/0224510 | A1 | 9/2011 | Oakhill |
| 2012/0238800 | A1* | 9/2012 | Naujokat ............. A61B 5/318 600/26 |
| 2013/0123571 | A1 | 5/2013 | Doman et al. |
| 2014/0081659 | A1 | 3/2014 | Nawana et al. |
| 2015/0073289 | A1* | 3/2015 | Lim ................. G16Z 99/00 600/529 |
| 2015/0073310 | A1 | 3/2015 | Pracar et al. |
| 2015/0359773 | A1 | 12/2015 | Feuerstein |
| 2017/0156662 | A1 | 6/2017 | Goodall et al. |
| 2018/0185318 | A1 | 7/2018 | Feuerstein |
| 2019/0021641 | A1 | 1/2019 | Feuerstein |

FOREIGN PATENT DOCUMENTS

| CN | 102188466 A | 9/2011 |
| WO | WO 00/44361 A2 | 8/2000 |
| WO | WO 2007/148308 A2 | 12/2007 |
| WO | WO 2011/100550 A2 | 8/2011 |
| WO | WO 2011/128635 A2 | 10/2011 |
| WO | WO 2014/052394 A1 | 4/2014 |

OTHER PUBLICATIONS

U.S. Appl. No. 16/067,277, filed Jun. 29, 2018, Feuerstein.
EP 13841071.7, May 3, 2016, Partial Supplementary European Search Report.
EP 138410717, Aug. 25, 2016, Extended European Search Report.
PCT/US2016/069484, Mar. 3, 2017, Invitation to Pay Additional Fees.
PCT/US2016/069484, May 9, 2017, International Search Report and Written Opinion.
PCT/US2016/069484, Jul. 12, 2018, International Preliminary Report on Patentability.
PCT/US2013/061588, Mar. 5, 2014, International Search Report and Written Opinion.
PCT/US2013/061588, Apr. 9, 2015, International Preliminary Report on Patentability.
Partial Supplementary European Search Report for European Application No. EP 13841071.7 dated May 3, 2016.
Extended European Search Report for European Application No. EP 13841071.7 dated Aug. 25, 2016.
Invitation to Pay Additional Fees for International Application No. PCT/US2016/069484 dated Mar. 3, 2017.
International Search Report and Written Opinion for International Application No. PCT/US2016/069484 dated May 9, 2017.
International Preliminary Report on Patentability for International Application No. PCT/US2016/069484 dated Jul. 12, 2018.
International Search Report and Written Opinion for International Application No. PCT/US2013/061588 dated Mar. 5, 2014.

(Continued)

*Primary Examiner* — Thaddeus B Cox
(74) *Attorney, Agent, or Firm* — Wolf, Greenfield & Sacks, P.C.

(57) ABSTRACT

Pharmaceutical combinations and methods for using such combinations to treat depression are disclosed. In various embodiments (he pharmaceutical combinations include combinations of omega-3 fatty acids, pharmacological sleep agents, and non-pharmacological sleep therapies, and may include other ingredients such as antidepressants. The present invention relates pharmaceutical combinations and methods for their use to treat depression.

20 Claims, No Drawings

(56) References Cited

OTHER PUBLICATIONS

International Preliminary Report on Patentability for International Application No. PCT/US2013/061588 dated Apr. 9, 2015.
Espie et al., A Randomized, Placebo-Controlled Trial of Online Cognitive Behavioral Therapy for Chronic Insomnia Disorder Delivered via an Automated Media-Rich Web Application. Sleep. 2012;35(6):769-81.
Ji et al., Effects of paroxetine with or without zolpidem on depression with insomnia: a multi-center randomized comparazive study. PubMed—NCBI. Jan. 1, 2007:1585-9.
Manber et al., Cognitive Behavioral Therapy for Insomnia Enhances Depression Outcome in Patients with Comorbid Major Depressive Disorder and Insomnia. Sleep. 2008;31(4):489-95.
Taylor et al., A Pilot Study of Cognitive-Behavioral Therapy of Insomnia in People with Mild Depression. Behavior Therapy. 2007;38:49-57.

* cited by examiner

COMBINATION METHODS AND COMPOSITIONS INCLUDING SLEEP THERAPEUTICS FOR TREATING MOOD

RELATED APPLICATION DATA

This application is a continuation of U.S. application Ser. No. 15/909,923, filed Mar. 1, 2018, now U.S. Pat. No. 10,758,508, entitled "COMBINATION METHODS AND COMPOSITIONS INCLUDING SLEEP THERAPEUTICS FOR TREATING MOOD", which is a continuation of U.S. patent application Ser. No. 14/431,399, filed Mar. 26, 2015, now abandoned, entitled "COMBINATION METHODS AND COMPOSITIONS INCLUDING SLEEP THERAPEUTICS FOR TREATING MOOD", which is a national stage filing under 35 U.S.C. § 371 of International Patent Application No. PCT/US2013/061588, filed Sep. 25, 2013, entitled "COMBINATION METHODS AND COMPOSITIONS INCLUDING SLEEP THERAPEUTICS FOR TREATING MOOD", which claims the benefit, under 35 U.S.C. § 119(e), of U.S. Provisional Patent Application No. 61/705,669, filed Sep. 26, 2012, entitled "COMBINATION METHODS AND COMPOSITIONS INCLUDING SLEEP THERAPEUTICS FOR TREATING MOOD", the entire contents of all of which are incorporated herein by reference in their entireties.

FIELD OF THE INVENTION

The present invention relates pharmaceutical combinations and methods to treat depression.

BACKGROUND OF RELATED TECHNOLOGY

Antidepressants are a well-known class of pharmaceuticals. They are generally categorized according to their mechanism of action on neurotransmitter activity (e.g., Selective Serotonin Reuptake Inhibitors; Serotonin and Norepinephrine Reuptake Inhibitors; Tricyclic antidepressants; and Monoamine Oxidase inhibitors); with a number of drugs in each category having received marketing approval in the U.S. and elsewhere. Although widely used, antidepressants are known to have a number of drawbacks. For example, they are known to be plagued by long delays in initiating response (typically 4 or more weeks), and may have only a partial or no response.

Certain natural compounds have also been investigated for their effectiveness in treating depression. For example, substantial work has been done to study the effectiveness of various omega-3 fatty acids in treating depression (See, for example, Carlezon et al., 2005; Marangell et al., 2003; U.S. Pat. Nos. 6,852,870, 8,071,646, and 8,372,451; and U.S. Patent Publ. Nos. 2005/0267212 and 2011/0200690).

Despite this work, however, the use of omega-3 fatty acids in treating depression has failed in clinical trials (e.g., VASCEPA® (icospent ethyl), an EPA-only omega-3 fatty acid, failed in depression clinical trials), and currently no omega-3 fatty acid formulation has been approved by the U.S. Food and Drug Administration (FDA) for use in treating depression. In fact, recent meta-analyses suggest omega-3 fatty acids, on a population level, have mixed results (See, for example, Mischoulon, 2011; Appleton et al., 2010; Martins, 2009; and Young and Conquer, 2005).

Insomnia has traditionally been thought to be associated with depression. As such, certain sleep medications have been used to treat sleep difficulties associated with depression. However, not only do these medications not treat the depression itself, findings suggest that they may actually cause and/or exacerbate depression (Kripke, 2007; and Walling, 2010).

In this regard, the FDA has required the side effect "worsening of depression" to be included on the label of certain sleep medications (such as zolpidem), and this side effect known to be associated with the use of sleeping pills has been receiving increased attention in the media (See, for example, Rabin, 2012). In fact, sleep deprivation—rather than sleep inducement—has been shown to help alleviate depression (See, for example, Giedke, 2002 which teaches that sleep deprivation may be help depression; See also, Giedke et al., 2003; Wirz-Justice, 1999; Adrien, 2002; Letemendia, 1986; and Wu, 1990). As such, sleep-inducing medications may be contraindicated in patients suffering from depression.

Thus, there is a need in the art for new treatments for depression, in particular for new pharmaceutical combinations to provide more robust treatments for depression with faster onset.

SUMMARY OF THE INVENTION

Accordingly, the present invention provides compositions, combinations and methods that overcome these and other problems, and provide a more robust treatment for depression with faster onset.

In certain exemplary, non-limiting embodiments, the present invention is directed to a pharmaceutical composition comprising an omega-3 fatty acid formulation and a sleep-inducing agent.

In certain exemplary, non-limiting embodiments, the omega-3 fatty acid formulation has greater than 90% purity.

In certain exemplary, non-limiting embodiments, the present invention is directed to a pharmaceutical composition comprising an omega-3 fatty acid formulation and a sleep-inducing agent, wherein the composition is substantially free of an antidepressant.

In certain exemplary, non-limiting embodiments, the present invention is directed to a combined pharmaceutical product for the treatment of depression, the product comprising, in combination: (i) first dose of an omega-3 fatty acid formulation and (ii) a second dose of a sleep-inducing agent, wherein the combination of the doses is effective for the treatment of depression in a patient in need thereof.

In certain exemplary, non-limiting embodiments, the present invention is directed to a combined pharmaceutical product for the treatment of depression, the product comprising, in combination: (i) first dose of an omega-3 fatty acid formulation and (ii) a second dose of a sleep-inducing agent, wherein the combination of the doses is effective for the treatment of depression in a patient in need thereof, and further wherein the combined pharmaceutical product further comprises instructions for administering each of the first dose and the second dose.

In certain exemplary, non-limiting embodiments, the present invention is directed to a method of treating depression comprising the administration of an anti-depressant effective amount of a combination of an omega-3 fatty acid formulation and a sleep-inducing agent to a patient in need thereof.

In certain exemplary, non-limiting embodiments, the present invention is directed to a method of treating depression comprising the administration of an anti-depressant effective amount of a combination of an omega-3 fatty acid formulation and a sleep-inducing agent to a patient in need thereof in the absence of an antidepressant.

In certain exemplary, non-limiting embodiments, the present invention is directed to a method of treating depression comprising the administration of an anti-depressant effective amount of a combination of an omega-3 fatty acid formulation and a sleep-inducing agent to a patient in need thereof, wherein the combination is effective for the treatment of depression even in the absence of an antidepressant.

In other certain exemplary, non-limiting embodiments, the present invention is directed to a pharmaceutical composition comprising an antidepressant and a sleep-inducing agent.

In other certain exemplary, non-limiting embodiments, the present invention is directed to a pharmaceutical composition comprising an antidepressant and a sleep-inducing agent which is substantially free of an omega-3 fatty acid formulation.

In other certain exemplary, non-limiting embodiments, the present invention is directed to a combined pharmaceutical product for the treatment of depression, the product comprising, in combination: (i) first dose of an antidepressant and (ii) a second dose of a sleep-inducing agent, wherein the combination of the doses is effective for the treatment of depression in a patient in need thereof.

In other certain exemplary, non-limiting embodiments, the present invention is directed to a combined pharmaceutical product for the treatment of depression, the product comprising, in combination: (i) first dose of an antidepressant and (ii) a second dose of a sleep-inducing agent, wherein the combination of the doses is effective for the treatment of depression in a patient in need thereof, and further wherein the combined pharmaceutical product further comprises instructions for administering each of the first dose and the second dose.

In certain exemplary, non-limiting embodiments, the present invention is directed to a method of treating depression comprising the administration of an anti-depressant effective amount of a combination of an antidepressant and a sleep-inducing agent to a patient in need thereof.

In certain exemplary, non-limiting embodiments, the present invention is directed to a method of treating depression comprising the administration of an anti-depressant effective amount of a combination of an antidepressant and a sleep-inducing agent to a patient in need thereof in the absence of an omega-3 fatty acid formulation.

In certain exemplary, non-limiting embodiments, the present invention is directed to a method of treating depression comprising the administration of an anti-depressant effective amount of a combination of an antidepressant and a sleep-inducing agent to a patient in need thereof, wherein the combination is effective for the treatment of depression even in the absence of an omega-3 fatty acid formulation.

In certain exemplary, non-limiting embodiments, the antidepressant is selected from the group consisting of tricyclic antidepressants, selective serotonin reuptake inhibitors (SSRI's), selective serotonin norepinephrine reuptake inhibitors, norepinephrine dopamine reuptake inhibitors and alpha-2 antagonist/serotonin 5HT2-3 receptor antagonists.

In certain exemplary, non-limiting embodiments, the antidepressant is a tricyclic antidepressant selected from the group consisting of selected from the group consisting trazodone, doxepin, amitriptyline, amoxapine, clomipramine, desipramine, doxepin, imipramine, maprotiline, nortriptyline, protriptyline and trimipramine, provided that if the antidepressant is trazodone it cannot also comprise the sleep-inducing agent.

In certain exemplary, non-limiting embodiments, the tricyclic antidepressant is selected from the group consisting of doxepin, amitriptyline, amoxapine, clomipramine, desipramine, doxepin, imipramine, maprotiline, nortriptyline, protriptyline and trimipramine.

In certain exemplary, non-limiting embodiments, the antidepressant is a selective serotonin reuptake inhibitor selected from the group consisting of citalopram, escitalopram, femoxetine, fluoxetine, fluvoxamine, paroxetine, sertraline and zimeldine.

In certain exemplary, non-limiting embodiments, the antidepressant is a selective serotonin reuptake inhibitor selected from the group consisting of duloxetine, venlafaxine, desvenlafaxine, milnacipran and clovoxamine.

In certain exemplary non-limiting embodiments, the antidepressant is a norepinephrine dopamine reuptake inhibitor.

In certain exemplary, non-limiting embodiments, norepinephrine dopamine reuptake inhibitor antidepressant is bupropion.

In certain exemplary, non-limiting embodiments, the antidepressant is a alpha-2 antagonist/serotonin 5HT2-3 receptor antagonist.

In certain exemplary, non-limiting embodiments, the alpha-2 antagonist/serotonin 5HT2-3 receptor antagonist antidepressant is mirtazapine.

In certain exemplary, non-limiting embodiments, the sleep-inducing agent is selected from the group consisting of antihistamines, hypnotics, trazadone tricyclic antidepressant, melatonin, melatonin receptor agonists, tryptophan and Valerian root.

In certain exemplary, non-limiting embodiments, the sleep-inducing agent is selected from the group consisting antihistamines, hypnotics, trazadone tricyclic antidepressants, melatonin, melatonin receptor agonists and Valerian root.

In certain exemplary, non-limiting embodiments, the sleep-inducing agents are selected from the group consisting of antihistamines, hypnotics, melatonin, melatonin receptor agonists, and Valerian root.

In certain exemplary, non-limiting embodiments, the sleep-inducing agent is selected from the group consisting of hypnotics, melatonin, melatonin receptor agonists, and Valerian root.

In certain exemplary, non-limiting embodiments, the sleep-inducing agent is selected from the group consisting of hypnotics, melatonin and melatonin receptor agonists.

In certain exemplary, non embodiments, the sleep-inducing agent is a hypnotic.

In certain exemplary, non-limiting embodiments, the hypnotics are selected from the group consisting of benzodiazepine hypnotics and non-benzodiazepine hypnotics.

In certain exemplary, non-limiting embodiments, the benzodiazepine hypnotics are selected from the group consisting of alprazolam, brotizolam, clonazepam, cinolazepam, diazepam, estazolam, etizolam, flunitrazepam, flurazepam, loprazolam, lormetazepam, nimetazepam, qauzepam temazepam and triazolam.

In certain exemplary, non-limiting embodiments, the non-benzodiazepine hypnotics are selected from the group consisting of imidazopyridines non-benzodiazepine hypnotics, pyrazolopyrimidines non-benzodiazepine hypnotics, cycloprrolones non-benzodiazepine hypnotics and β-carboline non-benzodiazepine hypnotics.

In certain exemplary non-limiting embodiments, the imidazopyridines non-benzodiazepine hypnotics are selected from the group consisting of zolpidem (tartrate), alpidem, necopidem and saripidem.

In certain exemplary, non-limiting embodiments, the pyrazolopyrimidines non-benzodiazepine hypnotics selected from the group consisting of zaleplon, divaplon, fasiplon, indiplon, lorediplon, ocinaplon, panadiplon and taniplon.

In certain exemplary, non-limiting embodiments, the cyclopyrrolones non-zodiazepine hypnotics are selected from the group consisting of eszopiclone, zopiclone, pagoclone, pazinaclone, suproclone and suriclone.

In certain exemplary, non-limiting embodiments, the β-carboline non-benzodiazepine hypnotics are selected from the group consisting of abecarnil and gedocarnil.

In certain exemplary, non-limiting embodiments, the omega-3 fatty acid formulation comprise EPA and DHA in a weight to weight ratio from about 3.5:1 to about 699 to 1.

In certain exemplary, non-limiting embodiments, the omega-3 fatty acid formulation comprise EPA and DHA in a weight to weight ratio from about 4.01:1 to about 6.99:1.

In certain exemplary, non-limiting embodiments, the omega-3 fatty acid formulation comprise EPA and DHA in a weight to weight ratio from about 4.01:1 to about 5:1.

In certain exemplary, non-limiting embodiments, the omega-3 fatty acid formulation comprise EPA and DHA in a weight to weight ratio of EPA:DHA is approximately 4.09:1.

In certain exemplary, non-limiting embodiments, the omega-3 fatter acid formulation comprise EPA and DHA, when taken together, is greater than 90% of the formulation by weight.

In certain exemplary, non-limiting embodiments, the omega-3 fatty acid formulation comprise EPA and DHA, when taken together, is greater than 91% of the formulation by weight.

In certain exemplary, non-limiting embodiments, the present invention is directed to a method of treating depression comprising the administration of an insomnia therapy program to a patient suffering from depression.

In certain exemplary, non-limiting embodiments, the present invention is directed to a method of treating depression comprising the administration of an insomnia, therapy program to a patient suffering from depression and further comprising administration to the patient an antidepressant in an amount effective to treat depression in combination with the insomnia therapy program.

In certain exemplary, non-limiting embodiments, the present invention is directed to a method of treating depression comprising the administration of an insomnia therapy program for to a patient suffering from depression and further comprising administration to the patient an omega-3 fatty acid formulation in an amount effective to treat depression in combination with the insomnia therapy program.

In certain exemplary, non-limiting embodiments, the present invention is directed to a method of treating depression comprising the administration of an insomnia therapy program to a patient suffering from depression and further comprising administration to the patient an antidepressant in an amount effective to treat depression in combination with the insomnia therapy program in the absence of administering a omega-3 fatty acid formulation.

In certain exemplary, non-limiting embodiments, the present invention is directed to a method of treating depression comprising the administration of an insomnia therapy program for to a patient suffering from depression and further comprising administration to the patient an omega-3 fatty acid formulation in an amount effective to treat depression in combination with the insomnia therapy program in the absence of administering an antidepressant.

In certain exemplary, non-limiting embodiments, the present invention is directed to a method of treating depression comprising the administration of an insomnia, therapy program to a patient suffering from depression, either alone or in combination with administration of one or more antidepressants and/or an omega-3 fatty acid formulation to the patient.

In certain exemplary, non-limiting embodiments, depression is treatment resistant depression.

In certain exemplary, non-limiting embodiments, treatment of depression or treatment-resistant depression is a 50% or greater reduction in a depression ratings scale score over the course of clinical treatment from starting point to endpoint depression symptoms rating scales.

In certain exemplary, non-limiting embodiments, depression symptoms rating scales are selected from the group consisting of $HRSD_{17}$, $QIDS\text{-}SR_{16}$ and MADRS.

In certain exemplary, non-limiting embodiments, the treatment of depression or treatment resistant depression comprises the depression going into remission.

In certain exemplary, non-limiting embodiments, the treatment of depression or treatment resistant depression comprises the patient achieving less than or equal to 7 on the $HRSD_{17}$ scale.

In certain exemplary, non-limiting embodiments, the treatment of depression or treatment resistant depression comprises the patient achieving less than or equal to 5 on the $QIDS\text{-}SR_{16}$.

In certain exemplary, non-limiting embodiments, the treatment of depression or treatment resistant depression comprises the patient achieving than or equal to 10 on the MADRS.

In certain exemplary, non-limiting embodiments, the patient is pregnant.

In certain exemplary, non-limiting embodiments, the treatment of depression or treatment-resistant depression occurs within about 8 weeks of first treatment, about 7 weeks of first treatment, about 6 weeks of first treatment, about 5 weeks of first treatment, about 4 weeks of first treatment, about 3 weeks of first treatment, about 2 weeks of first treatment or about 1 week of first treatment.

In certain exemplary, non-limiting embodiments, onset of the attenuation of depression or treatment-resistant depression occurs within about 8 weeks of first treatment, about 7 weeks of first treatment, about 6 weeks of first treatment, about 5 weeks of first treatment, about 4 weeks of first treatment, about 3 weeks of first treatment, about 2 weeks of first treatment or about 1 week of first treatment.

Other exemplary, non-limiting embodiments provide a pharmaceutical combination comprising an omega-3 fatty acid and a sleep-inducing agent. The combination includes embodiments in which the omega-3 fatty acid and sleep-inducing agent are in separate dosage forms, but provided together, for example in a single package.

In certain embodiments the purity of the omega-3 fatty acid is greater than 90%. The disclosure also provides pharmaceutical combination comprising an antidepressant and a sleep-inducing agent. The antidepressant and sleep-inducing agent may be provided together, but as separate dosage forms, or may comprise a single dosage form, e.g. as a pharmaceutical formulation.

In certain exemplary, non-limiting embodiments, the present invention is directed to methods of treating depression comprising the administration of a non-benzodiazepine hypnotic to a patient in need thereof.

In certain exemplary, non-limiting embodiments, the present invention is directed to methods of treating depression comprising the administration of a non-benzodiazepine hypnotic to a patient in need thereof wherein said a non-benzodiazepine hypnotic is selected from the group consisting of zolpidem (tartrate) and eszopiclone.

In certain exemplary, non-limiting embodiments the sleep-inducing agent is selected from trazodone, diphenhydramine, zolpidem, eszopiclone, tryptophan, and melatonin. In other embodiments the sleep-inducing agent is a benzodiazepine.

In other exemplary, non-limiting embodiments, one or more of the above embodiments (or elements within the embodiments) are suitably combined. By way of illustration, such an embodiment could reflect the combination of the embodiment directed to "a method of treating depression comprising the administration of an anti-depressant effective amount of a combination of an omega-3 fatty acid formulation and a sleep-inducing agent to a patient in need thereof" and the embodiment directed to "the treatment of depression or treatment resistant depression comprises the patient achieving less than or equal to 7 on the $HRSD_{17}$ scale."

In other exemplary, non-limiting embodiments, the elements comprising one or more of the embodiments herein are independent of each other such that one or more of the elements may be suitably excluded to comprise an additional embodiment thereof that is a subset of the original embodiment. By way of illustration, the embodiments recited herein defining benzodiazepine hypnotics as being "selected from the group consisting of alprazolam, brotizolam, clonazepam, cinolazepam, diazepam, estazolam, etizolam, flunitrazepam, flurazepam, loprazolam, lormetazepam, nimetazepam, qauzepam temazepam and triazolam" also represent an embodiment to a subset or sub-combination thereof, e.g. "selected from the group consisting of alprazolam, brotizolam and clonazepam" or any other suitable subset.

DETAILED DESCRIPTION OF THE INVENTION

Generally speaking, and as discussed in greater detail in the illustrative and non-limiting Examples provided herein, the present invention is directed to pharmaceutical compositions and methods for their use to treat depression. In various described exemplary, non-limiting embodiments, the pharmaceutical compositions include combinations of omega-3 fatty acids, pharmacological sleep agents, and non-pharmacological sleep therapies, and may include other ingredients such as antidepressants. For example, certain exemplary, non-limiting embodiments, the present invention include (1) a pharmaceutical composition comprising an omega-3 fatty acid formulation and a sleep-inducing agent (2) a pharmaceutical composition comprising an omega-3 fatty acid formulation and a sleep-inducing agent, wherein the composition is substantially free of an antidepressant (3) a pharmaceutical composition comprising an omega-3 fatty acid formulation and a sleep-inducing agent, wherein the composition further comprises an antidepressant (4) a pharmaceutical composition comprising an an antidepressant and a sleep-inducing agent (5) a pharmaceutical composition comprising an an antidepressant and a sleep-inducing agent, wherein the composition is substantially free of an omega-3 fatty acid formulation (6) a pharmaceutical composition comprising an antidepressant and a sleep-inducing agent, wherein the composition further comprises an omega-3 fatty acid formulation (7) methods of treating depression comprising the administration of the above examples to a patient in need thereof (8) a method of treating depression comprising the administration of an insomnia therapy program to a patient suffering from depression (9) a method of treating depression comprising the administration of an insomnia therapy program to a patient suffering from depression further comprising administration to the patient an antidepressant in an amount effective to treat depression in combination with said insomnia therapy program (10) a method of treating depression comprising the administration of an insomnia, therapy program to a patient suffering from depression further comprising administration to the patient an omega-3 fatty acid formulation in an amount effective to treat depression in combination with said insomnia therapy program and (11) a method of treating depression comprising the administration of an insomnia therapy program to a patient suffering from depression further comprising administration to the patient an omega-3 fatty acid formulation and an antidepressant in an amount effective to treat depression in combination with said insomnia therapy program.

Various definitions are provided herein, explicitly and/or through usage, and it is understood that such definitions will be applied by those of skill in the art in understanding the present invention.

The terms "a" and "an" do not denote a limitation of quantity, but rather denote the presence of at least one of the referenced item.

An "active agent" means any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. All stereoisomers, diastereomers, Z- and E-forms, in purified and mixture forms are included. Accordingly, when a compound is recited by specific name or a class of compounds is recited, all these forms are intended to be included. By illustration, active agents as provided herein include, for example, antidepressants, omega-3 fatty acid formulations and sleep-inducing agents.

A "dosage form" is any unit of administration ("unit dose") of one or more active agents. As such, a "pharmaceutical composition" as used herein may be presented in the form of a dosage form or unit dose and may comprise one or more active agents. Thus, a pharmaceutical composition as used herein could, for example, provide two active agents admixed together in a unit dose or provide two active agents combined in a dosage form wherein the active agents are physically separated and/or have different release rates. Pharmaceutical compositions include any suitable formulation including, for example, capsules, tablets, injections and liquids and may be administered through any suitable route including oral, buccal, parenteral, intravenous, intramuscular, rectal, transdermal and the like. Excipients used to formulate the pharmaceutical formulations may be any of those suitable for the respective dosage form such as fillers, stabilizers, extenders, binders, humidifiers, surfactants, lubricants, and the like. A "combined pharmaceutical product" as used herein is a combination of two more doses of two or more different active agents combined in separate dosage forms which are not admixed.

"Therapeutically effective amount" and/or "effective amount" means an amount effective, when administered to a human or non-human patient, to provide any therapeutic benefit. A therapeutic benefit may be an amelioration of symptoms, e.g., an amount effective to decrease the symptoms of binge-eating disorder or a major depressive disorder. In certain circumstances a patient may not present symptoms of a condition for which the patient is being treated. Thus a therapeutically effective amount of a compound is also an amount sufficient to provide a significant positive effect on any indicia of a disease, disorder or condition e.g. an amount sufficient to significantly reduce the frequency and severity of binge eating behavior or depressive symptoms. A significant effect on an indicia of a disorder or condition includes a statistically significant in a standard parametric test of statistical significance such as Student's T-test, where p<0.05; though the effect need not be significant in some embodiments. "Patient" as used herein means human or non-human animals.

Frequency of dosage may vary depending on the compound used and the particular type of depression treated. For most disorders a dosage regimen of once per day is preferred. Dosage regimens in which the active agent, whether omega-3 fatty acid, antidepressant, or sleep-inducing agent is administered 2 times daily may occasionally be more helpful.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease in the patient undergoing therapy. Patients may generally be monitored for therapeutic effectiveness using assays suitable for the condition being treated or prevented, which will be familiar to those of ordinary skill in the art.

Moreover, for each of the sleep-inducing agent(s), antidepressant(s) and omega-3 fatty acid formulation(s), the dose needed for use in the inventive compositions and combinations to effectively treat depression may, in certain embodiments, be lower than the dose needed to effectively treat depression when used alone (this lower dose may be referred to herein as a "suboptimal" dose, in that it is below an amount that is required for each of these ingredients to reach optimal therapeutic effect for any given patient when used alone). For example, in certain embodiments of the present invention, the dose of an antidepressant needed to effectively treat a patient's depression is lower when the antidepressant is used together with a non-benzodiazepine hypnotic (in a composition or combination, as taught herein) than when the antidepressant is used alone. Similarly, for each of the sleep-inducing agent(s), antidepressant(s) and omega-3 fatty acid formulation(s), the dose needed for use in combination with an insomnia therapy program to effectively treat depression may be lower than the dose needed to effectively treat depression when used alone. Thus, without being bound to any particular theory, the use of two or more of the following: sleep-inducing agent(s), antidepressant(s), omega-3 fatty acid formulation(s) and insomnia sleep therapy program(s), in various embodiments of the present invention has been found to be surprisingly effective in treating depression.

Depression includes depressive disorders listed in the American Psychiatric Association's Diagnostic and Statistical Manual of Mental Disorders (DSM-V); such as major depressive disorder, dysthymic disorder, and depressive disorder not otherwise specified (for instance, premenstrual dysphoric disorder). In certain embodiments the depression is treatment-resistant depression. "Treatment-resistant depression" as used herein indicates patients who do not respond to two separate trials of different antidepressants of adequate dose and duration in the current episode.

Depression may be considered effectively treated when a patient's symptoms, as measured by a depression symptom rating scale, improve.

"Depression symptoms rating scale" refers to any one of a number of standardized questionnaires, clinical instruments, or symptom inventories utilized to measure symptoms and symptom severity in depression. Such rating scales are often used in clinical studies to define treatment outcomes, based on changes from the study's entry point(s) to endpoint(s). Such depression symptoms rating scales include, but are not limited to, The Quick Inventory of Depressive-Symptomatology Self-Report (QIDS-SR$_{16}$), the 17-Item Hamilton Rating Scale of Depression (HRSD$_{17}$), the 30-Item Inventory of Depressive Symptomatology (IDS-C$_{30}$), or The Montgomery-Asperg Depression Rating Scale (MADRS) and Beckman Depression Inventory II. Such ratings scales may involve patient self-report or be clinician rated. A 50% or greater reduction in a depression ratings scale score over the course of a clinical trial (starting point to endpoint) is typically considered a favorable response for most depression symptoms rating scales. "Remission" in clinical studies of depression often refers to achieving at, or below, a particular numerical rating score on a depression symptoms rating scale, i.e., less than or equal to 7 on the HRSD$_{17}$; or less than or equal to 5 on the QIDS-SR$_{16}$; or less than or equal to 10 on the MADRS or less than or equal to 9 on the Beck Depression Inventory II. An alternative measure commonly used to assess depression and response is the Patient Health Questionnaire No. 9 (PHQ-9). A reduction in the score is generally used as a measure of improvement and the score level is used to estimate none, mild, moderate or severe disease categories. Moving from one category to another is generally considered significant change. As such treatment of depression or treatment-resistant depression may be evidenced by an improvement to the patient progressing to next less severe PHQ-9 category after treatment which is termed "PHQ-9 categorical improvement" as used herein.

As used herein, "sleep-inducing compounds" and/or "sleep-inducing agents" include the following: (1) antihistamines such as BENADRYL® (diphenhydramine), (2) "hypnotics" which include (a) benzodiazepines such as alprazolam, brotizolam, clonazepam, cinolazepam, diazepam, estazolam, etizolam, flunitrazepam, flurazepam, loprazolam, lormetazepam, nimetazepam, qauzepam temazepam, and HALCION® (triazolam), (b) "non-benzodiazepine hypnotics" also known as Z-drugs such as (i) "imidazopyridines" including AMBIEN (CR)® zolpidem (tartrate), alpidem, necopidem and saripidem (ii) "pyrazolopyrimidines" such as zaleplon, divaplon, fasiplon, indiplon, lorediplon, ocinaplon, panadiplon and taniplon (iii) "cyclopyrrolones" such as LUNESTA® (eszopiclone), IMOVANE® (zopiclone), pagoclone, pazinaclone, suproclone and suriclone and (iv) β-carbolines such as abecarnil, gedocarnil (3) certain tricyclic antidepressants including DESYREL® (trazodone), (4) melatonin and melatonin receptor agonists such as ramelteon and (5) other sleep-inducing agents such as tryptophan and Valerian root and melatonin.

The term "antidepressant" as used herein includes (1) tricyclic antidepressants including DESYREL® (trazodone), doxepin, amitriptyline, amoxapine, clomipramine, desipramine, doxepin, imipramine, maprotiline, nortriptyline, protriptyline, and trimipramine; (2) selective serotonin reuptake inhibitors (SSRIs) including citalopram, escitalopram, femoxetine, fluoxetine, fluvoxamine, paroxetine, sertraline, and zimeldine; selective serotonin norepinephrine reuptake inhibitors including duloxetine, venlafaxine, desvenlafaxine, milnacipran, and clovoxamine; (3) norepinephrine dopamine reuptake inhibitors such as bupropion; and (4) alpha-2 antagonist/serotonin 5HT2-3 receptor antagonists such as mirtazapine.

Wherein embodiments of the present invention comprise both an antidepressant and a sleep-inducing agent, the antidepressant and the sleep-inducing agent are different compounds. For example, trazadone is known in the art both as an antidepressant and as a sleep-inducing agent. Accordingly, an embodiment of the present invention that is directed to a pharmaceutical composition including both an antidepressant and a sleep-inducing agent may include trazadone as either the antidepressant or as the sleep-inducing agent, but not both.

As used herein, an "omega-3 fatty acid formulation" includes EPA and/or DHA. More particularly, an omega-3 fatty acid formulation according to the present invention may comprise EPA and DHA in a weight to weight ratio from about 3.5:1 to about 6.99 to 1, from about 4.01:1 to about 6.99:1, or from about 4.01:1 to about 5:1. The present invention also provides a highly purified omega-3 fatty acid formulation in which the weight to weight ratio of EPA:DHA is approximately 4.09:1. The EPA and DHA may be present in the formulation in either the triglyceride form or in the form of esterified fatty acid. Capsules typically contain the ethyl esters forms of EPA and DHA. Candy formulations typically contain the triglyceride forms of EPA and DHA.

The present invention also provides highly purified omega-3 fatty acid formulations in which the content of EPA and DHA, taken together, is greater than about 70%, greater than about 75%, greater than about 84%, or greater than about 85% of the formulation by weight, and the omega-3 fatty acids comprise greater than about 85%, greater than about 90%, or greater than about 91% of the formulation by weight. Additionally the present invention provides omega-3 fatty acid formulations in which the amount of cholesterol in the formulation is less than about 5% by weight, less than about 2.5% by weight, or less than about 1% by weight. The present invention also includes omega-3 fatty acid formulations in which the formulation comprises less than about 20 milliequivalents per kg peroxides, less than about 10 milliequivalents per kg peroxides, or less than about 5 milliequivalents per kg peroxides. See also U.S. Pat. No. 8,071,646, incorporated in its entirety by reference herein.

As discussed herein, in certain embodiments the present invention is directed methods of treating depression by administering an insomnia therapy program to a patient suffering from depression (alone or in combination with one or more antidepressants and/or an omega-3 fatty acid formulation).

As used herein, the term "insomnia therapy program" refers to a non-pharmacological, computer-implemented cognitive behavioral therapy program useful for treating insomnia in a patient. The terms "insomnia, therapy program," "insomnia talk therapy program," and "talk therapy program for insomnia" may be used interchangeably herein.

One example of an insomnia therapy program that may be used in the present invention includes the program described in Vincent and Lewycky, 2009 and Vincent et al., 2009, the entirety of each of which is hereby incorporated by reference. While such programs have been shown to be effective for treating insomnia (See, for example, Vincent, 2009), they have not been used to treat depression.

In one embodiment, an insomnia therapy program used in the present invention includes a plurality of software modules with which the patient interacts over a network. The software modules are stored in a computer system which includes non-transitory computer readable medium for storing the software, and one or more processors for executing instructions contained in the software. The software modules may be web-based such that the patient interacts with the software modules over the Internet.

As set forth in Table 1, each software module is intended to affect a cognitive and/or behavioral change in the patient.

TABLE 1

Insomnia Therapy Program: Software Modules

| | |
|---|---|
| Module 1 | Includes psychoeducation about insomnia (e.g., information about normal sleep, types of sleep disorders). Presents the cognitive behavioral model of insomnia (Morin, 1993). Patient is instructed to avoid clock-watching to reduce hyperarousal in the bedroom. |
| Module 2 | Includes information regarding sleep hygiene (e.g., implication of daytime napping for sleep, information regarding effects of alcohol consumption on sleep) and stimulus control (e.g., encouragement to avoid engendering arousal in the bedroom environment, removing of oneself from bed if unable to sleep, going to bed only when sleepy). Patient is instructed to chose two habits to change. |
| Module 3 | Presents relaxation training and provides MP3 audio files for paced breathing, progressive muscle relaxation, imagery-induced relaxation, and self-hypnosis. Patient is instructed to practice relaxation strategies on daily basis, as well as to continue practicing sleep hygiene and stimulus control. Patient is asked to choose the relaxation exercises that they most liked and to practice with those. There is no demand to work on all 4 relaxation exercises concurrently. |
| Module 4 | Teaches sleep restriction (Spielman et al., 1987) and discusses how to gradually taper off hypnotic medications only under the direction of a physician. Patient is against tapering if they had comorbid medical conditions as a safety precaution. For SRT, patient is informed about how to calculate a sleep window but is discouraged from using this strategy if currently sleeping less than 4 hours per night. |
| Module 5 | Cognitive therapy, including instruction and modeling regarding the identification and correction of automatic thoughts that may increase arousal (Morin, 1993); instruction regarding scheduled problem solving (Dugas, 2003); and instruction and modeling regarding the downward arrow technique (Burns, 1980). Patient has the opportunity to listen to audio files of cognitive therapy between actors portraying patients with insomnia and the first author acting as cognitive therapist. Patient is instructed to monitor thoughts and attempt to replace anxiety-provoking thoughts with more realistic alternatives. |

The discussion herein and the following Examples set forth and illustrate various exemplary embodiments of the present invention, which are understood to be illustrative and non-limiting.

Example 1

Case Study 1: 38 Year Old Male

A 38 year old male patient seen for depression had taken a serotonin specific reuptake inhibitor, fluoxetine for four weeks without improvement. The patient was started on 20 mg daily for one month and this was increased to a maximum dose of 60 mg daily over the subsequent two months. The higher doses improved depression minimally Beck Depression Inventory II score change from 28 to 26 over three months of fluoxetine monotherapy.

Subsequently, addition of AMBIEN® at only 2.5 mg (one half of a 5 mg tablet) led to improvement in depression rating scales of 38% in 4 days after addition to the medical regimen. In this case, the depression was rated with the Beck Depression inventory II and at first visit the patient's score was 28 and at the upper end of the moderate range.

Over the course of the patient's treatment with fluoxetine as monotherapy, the patient's mood remained depressed with mild improvement to a Beck Depression Inventory II score of 26 after dose increases. When the AMBIEN® was added, the score improved an additional 8 points to 18, and the score for sleep was unchanged. At the time of this treatment course, the patient was also taking albuterol inhaler as needed for asthma and had no other active medical conditions or medications.

Example 2

Case Study 2: 44 Year Old Female

A 44 year old female patient presented with depression that had been unresponsive to three known antidepressants over the preceding year (fluoxetine; venlafaxine; and the tricyclic amitryptiline). A new trial of fluoxetine at 20 mg was started concurrently with LUNESTA® (dose: 2 mg at bedtime). Mood returned to normal/mild depression range based on PHQ-9 score. This showed efficacy because the PHQ-9 score before treatment initiation was 17 (indicating "moderately severe depression") and had dropped to 7 (indicating "mild depression") in six days at subsequent visit. This showed a shift of two categories in the PHO-9 scale. On the PHQ the patient rated their sleep problems as "not at all" when asked about trouble falling or staying asleep, or sleeping too much. Antidepressant effects are known to occur in 2-6 weeks when used as previously studied.

During the course of treatment this patient was utilizing birth control via NUVARING® monthly and was also prescribed alprazolam as needed for anxiety. Use of alprazolam was limited to plane flights and attending crowded social events.

Example 3

Case Study 3: 41 Year Old Male

A 41 year old male patient presented with no complaints of sleep difficulties but with complaints of depression that had been unresponsive to fluoxetine and citalopram. An omega-3 fatty acid formulation was started at 2 grams daily composed of a >90% pure omega-3 fatty acid formulation with a ratio of EPA:DHA of approximately 4:1 with AMBIEM® (5 mg at bedtime) and in 5 days mood showed significant improvement by patient report (patient reported no longer feeling depressed).

Questioning the patient evidenced no difficulty sleeping—either too much or too little—before the AMBIEN® is started. There remained no sleep complaints throughout the treatment course—either of which can occur with depression. During the course of treatment patient was also taking atorvastatin, 10 mg daily.

The above Examples surprisingly show and suggest inter alia that non-benzodiazepine hypnotics (which are known in the art to exacerbate depression) are effective in treating depression (including treatment-resistant depression) when combined with antidepressant(s) or omega-3 fatty acid(s).

Example 4

Case Study 4: 62 Year Old Male

A 62 year old male patient suffering from depression had failed trials of several medications including fluoxetine, citalopram, trazodone. In addition, the patient had taken ATIVAN® (lorazepam) on rare occasions related to anxiety inducing situations which also did not improve the patient's depression.

The patient was started on a trial of fluoxetine and ATIVAN® (lorazepam) regularly at bedtime (0.5 mg and an additional 0.5 mg as needed for dose of 1.0 mg) (Riemann, 2009) and the patient's mood improved, with rating scale improvements (PHQ-9 score from 22 to 10) of greater than 50% in one week of treatment.

This example surprisingly shows and suggests inter alia that benzodiazepine hypnotics (which have been shown in the art to have no significant effect in treating depression) are effective in treating depression (including treatment-resistant depression) when combined with antidepressant(s).

Example 5

Case Study 5: 35 Year Old Female

A 35 year old female patient with onset of depression in pregnancy was interested in natural remedies. The patient was started on an omega-3 fatty acid (OMAX-3®) with minimal effect after 4 weeks PHQ-9 score went from 17 to 16.

Two weeks later the patient's PHQ-9 remained at 16. The patient was not complaining of sleep difficulties, in fact described increased sleep. Despite this, Valerian (obtained from GNC®—which is known to help induce sleep (Gyllenhaal, 2000)—was added to the regimen (of OMAX-3®) at 500 mg one hour before bed. The patient described a desired bed time of ten PM and dose was taken at 9 PM.

One week later the patient described improved mood and the patient's PHQ-9 score improved to 11 despite the fact Valerian is a central nervous system depressant and is believed to cause mild depression (Houghton, 1999).

The above Example surprisingly shows and suggests inter cilia that sleep-inducing agents such as Valerian (which have not been shown in the art to be effective in treating depression) are effective in treating depression (including treatment-resistant depression) when combined with omega-3 fatty acid(s).

Example 6

Case Study 6: 36 Year Old Female

Onset of depression in pregnancy is common. In this 36 year old pregnant female patient who presented with new onset of depression, the patient's PHQ-9 score was 1.5 and the patient detailed no sleep complaints. The patient was concerned about taking any pharmaceutical and was initiated on an omega-3 fatty acid with high purity (>90% omega-3 and a ratio of EPA to DHA of approximately 4:1, sold as OMAX-3® and simultaneously started on an insomnia therapy program as described herein that provided cognitive behavioral therapy for insomnia over six weeks, despite a lack of insomnia complaints.

Specifically, the insomnia therapy program was organized into modules, and was offered as an internet-based application as a mix of interactive multimedia content, an interactive sleep diary, sleep restriction, and relaxation training. Module 1 included psychoeducation about insomnia (e.g., information about normal sleep, types of sleep disorders) and presented the cognitive behavioral model of insomnia. Module 2 included information regarding sleep hygiene (e.g., implication of daytime napping for sleep, information regarding effects of alcohol consumption on sleep) and stimulus control (e.g., encouragement to avoid engendering arousal in the bedroom environment, removing of oneself from bed if unable to sleep, going to bed only when sleepy). Module 3 presented relaxation, passive muscle relaxation, imagery-induced relaxation, and self-hypnosis. Participants were asked to choose the relaxation exercises that they most liked and to practice with those. There was no demand to work on all four relaxation exercises concurrently. Module 4 introduced the concept of sleep restriction. Module 5 introduced cognitive therapy, including correction of automatic thoughts that may increase arousal, instruction regarding scheduled problem solving, and instruction and modeling regarding the downward arrow technique. Module 6 were exercises in mindfulness meditation.

The patient's depression improved after 3 weeks to a PHQ-9 score of 4.

The above Example surprisingly shows and suggests inter alia that insomnia therapy programs when combined with omega-3 fatty acid(s) (which have not been shown in clinical trials to be effective in treating depression when administered independently) are effective in treating depression (including treatment-resistant depression) when co-administered.

Example 7

Case Study 7: Insomnia Therapy Program to Treat Depression in a Male Patient

A male patient with a history of depression presented and described a history of trying several antidepressants without success. The patient's PHQ-9 was 16 and the patient endorsed 9 hours of sleep, and rated the PHQ-9 sleep question at 0. The patient did, however, describe sleeping about 4 hours during the day and 5 hours at night. The patient was given a regimen of sleep hygiene and sleep restriction from an interactive insomnia therapy program as described herein.

Specifically, the program was a six module program which also tracked sleep metrics in a sleep diary. The modules focused on insomnia and goal setting, relaxation exercises, sleep restriction, mindfulness, cognitive restructuring and sleep hygiene. The patient continued to sleep 9 hours, but this shifted to all being at night as a result of the intervention. The patient's PHQ-9 score dropped to 4.

The above Example surprisingly shows and suggests inter alia that insomnia therapy programs (which have not been shown in the art to be effective in treating depression) are effective in treating depression (including treatment-resistant depression).

REFERENCES

Adrien, J. "Neurobiological bases for the relation between sleep and depression." *Sleep Med. Rev.* 6 (5):341-51 (October 2002).

Appleton, K. M., Rogers, P. J. and Andrew, R. N. "Updated systematic review and meta-analysis of the effects of n-3 long-chain polyunsaturated fatty acids on depressed mood." *Am. J. Clin. Nutr.* 91 (31):757-770 (2010).

Burns, D. D. *Feeling Good: The Mood Therapy Book.* New York: New American Library (1980).

Carlezon Sr., W. A., Mague, S. D., Paro A. M., Stoll, Cohen, B. M. and Renshaw, P. F. "Antidepressant-like effects of uridine and omega-3 fatty acids are potentiated by combined treatment in rats." *Biol. Psychiatry.* 57 (4):343-50 (Feb. 15, 2005).

Dugas, M. J., Ladouceur, R., Léger, E., Freeston, M. H., Langlois, F., Provencher, M. D. and Boisvert, J. M. "Group cognitive-behavioral therapy for generalized anxiety disorder: treatment outcome and long-term follow-up." *J. Consult. Clin. Psychol.* 71 (4):821-5 (August 2003)

Giedke H. "Therapeutic use of sleep deprivation in depression." *Sleep Med Rev.* 6 (5):361-77 (October 2002).

Giedke, H., Klingberg, S., Schwarzler, F. and Schweinsberg, M. "Direct comparison of total sleep deprivation and late partial sleep deprivation in the treatment of major depression," *J. Affect. Disord.* 76 (1-3):85-93 (September 2003).

Gyllenhaal, C., Merritt, S. L., Peterson, S. D., Block, K. I. and Gochenour, T. "Efficacy and safety of herbal stimulants and sedatives in sleep disorders." *Sleep Med Rev.* 4 (3):229-251 (June 2000).

Houghton, Y. J. "The scientific basis for the repined activity of Valerian." *J. Pharm. Pharmacol.* 51 (5):505-12 (May 1999).

Kripke, D. "Greater incidence of depression with hypnotic use than with placebo." *BMC Psychiatry* 7:42 (2007).

Letemendia, F. J. "Diagnostic applications of sleep deprivation." *Can. J. Psychiatry.* 31 (8):731-6 (November 1986).

Marangell, L. B., Martinez, J. M., Zboyan, H. A., Kertz, B., Kim, H. F. and Puryear, L. J. "A double-blind, placebo-controlled study of the omega-3 fatty acid docosahexaenoic acid in the treatment of major depression." *Am. J. Psychiatry.* 160 (5):996-8 (May 2003).

Martins, J. G. "EPA but not DHA appears to be responsible for the efficacy of omega-3 long chain polyunsaturated fatty acid supplementation in depression: evidence front a meta-analysis of randomized controlled trials." *J. Am. Coll. Nutr.* 28 (5):525-542 (2009).

Mischoulon, D. "The impact of omega-3 fatty acids on depressive disorders and suicidality: can we reconcile 2 studies with seemingly contradictory results'?" *J. Clin. Psychiatry.* 72 (12):1574-6 (December 2011).

Morin, C. M. *Insomnia: Psychological Assessment and Management,* New York: Guilford Press (1993).

Rabin, R. "New Worries About Sleeping Pills." *The New York Times* (Mar. 12, 2012) (available online at: http://well.blogs.nytimes.com/2012/03/12/new-worries-about-sleeping-pills).

Riemann, D. and Perlis, M. L. "The treatments of chronic insomnia: a review of benzodiazepine receptor agonists and psychological and behavioral therapies." *Sleep Med Rev.* 13 (3):205-14 (June 2009).

Spielman, A. J., Saskin, P. and Thorpy M. J. "Treatment of chronic insomnia by restriction of time in bed." *Sleep.* 10 (1):45-56 (February 1987).

U.S. Pat. No. 6,852,870.
U.S. Pat. No. 8,071,646.
U.S. Pat. No. 8,372,451.
United States Patent Publ. No. 2005/0267212.
United States Patent Publ. No. 2011/0200690.

Vincent, N. and Lewycky, S. "Logging on for better sleep: RCT of the effectiveness of online treatment for insomnia." *Sleep.* 32 (6):807-15 (June 2009).

Vincent, N., Lewycky, S., Hart Swain, K. and Holmqvist, M. "Logging on for Nodding Off: Empowering Individuals to Improve Their Sleep." *The Behavior Therapist.* 32 (6): 123-126 (September 2009).

Walling, J. "Eszopiclone improves Menopausal Symptoms." *Am. Fam. Physician.* 82 (5):528-531 (Sep. 1, 2010).

Wirz-Justice, A. "Sleep deprivation in depression: what do we know, where go?" *Biol. Psychiatry.* 46 (4):445-53 (Aug. 15, 1999).

Wu, J. C. "The biological basis of an antidepressant response to sleep deprivation and relapse: review and hypothesis." *Am. J. Psychiatry.* 147 (1):14-21 (January 1990).

Young, U. and Conquer. S. "Omega-3 fatty acids and neuropsychiatric disorders," *Reprod. Nutr. Dev.* 45 (1):1-28 (2005).

The present invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout the Specification and provided in a list of references above, each of which is incorporated herein by reference in its entirety. The citation of references herein shall not be construed as an admission that such is prior art to the present invention.

What is claimed is:

1. An apparatus offered or prescribed by a clinician for treating at least one mood disorder a patient is experiencing, the apparatus comprising:
    at least one processor configured to:
        receive at least one interaction from the patient;
        receive information relating to at least one sleep aspect from the patient and not indicating that the patient is complaining to the clinician about any sleep aspect; and
        treat the at least one mood disorder by outputting, to the patient, information assisting in treatment of the at least one sleep aspect based at least in part on the at least one interaction received from the patient,
    wherein the information assisting in the treatment of the at least one sleep aspect comprises at least one element of cognitive behavioral therapy for the at least one sleep aspect.

2. The apparatus of claim 1, wherein:
    the apparatus is connected to a network, and
    the apparatus is configured to:
        send the at least one interaction to at least one computer connected via the network; and
        receive the information assisting in the treatment of the at least one sleep aspect from the at least one computer,
        wherein the information assisting in the treatment of the at least one sleep aspect includes:
            psychological education material,
            relaxation training,
            interactive multimedia content for paced breathing, progressive muscle relaxation, imagery-induced relaxation, and/or self-hypnosis, and/or
            instructions on patient monitoring of and adjustment of thoughts of the patient.

3. The apparatus of claim 1, wherein:
    the at least one sleep aspect comprises a sleep disorder, a sleep pattern, a sleep quality, sleep timing, sleep duration, and/or a quality or quantity of sleep disruption.

4. The apparatus of claim 1, wherein:
    the information relating to the at least one sleep aspect comprises a sleep diary tracking at least one metric related to sleep behavior of the patient.

5. The apparatus of claim 1, wherein:
    the at least one processor is configured to receive information relating to the at least one mood disorder from the patient.

6. The apparatus of claim 1, wherein:
    the at least one mood disorder comprises at least moderate depression that is treatment-resistant.

7. The apparatus of claim 1, wherein:
    the at least one processor is configured to treat the at least one mood disorder by outputting the information assisting in treatment of the at least one sleep aspect and by causing administering to the patient an omega-3 fatty acid formulation or an antidepressant.

8. A system for treating a patient suffering from at least one mood disorder, the system comprising:
    at least one computer; and
    at least one apparatus connected to the at least one computer via at least one network, the at least one apparatus comprising:
        at least one processor configured to:
            receive at least one interaction from the patient;
            receive information relating to at least one sleep aspect from the patient and not indicating that the patient is complaining to the clinician about any sleep aspect; and
            treat the at least one mood disorder by outputting, to the patient, information assisting in treatment of the at least one sleep aspect based at least in part on the at least one interaction received from the patient,
    wherein the information assisting in the treatment of the at least one sleep aspect comprises at least one element of cognitive behavioral therapy for the at least one sleep aspect.

9. The system of claim 8, wherein:
    the information relating to the at least one sleep aspect comprises a sleep diary tracking at least one metric related to sleep behavior of the patient.

10. The system of claim 8, wherein:
    the information assisting in the treatment of the at least one sleep aspect comprises:
        psychological education material,
        relaxation training,
        interactive multimedia content for paced breathing, progressive muscle relaxation, imagery-induced relaxation, and/or self-hypnosis,
        instructions on patient monitoring of and adjustment of thoughts of the patient,
        an interactive sleep diary tracking at least one metric related to sleep behavior of the patient,
        instructions on modifying sleep behavior of the patient,
        information regarding sleep hygiene and stimulus control,
        instructions on sleep restriction and/or sleep windows, and/or
        instructions on use of medication.

11. The system of claim 8, wherein:
    the at least one mood disorder comprises at least moderate depression that is treatment-resistant.

12. The system of claim 8, wherein:
the at least one processor is configured to treat the at least one mood disorder by outputting the information assisting in treatment of the at least one sleep aspect and by causing administering to the patient an omega-3 fatty acid formulation or an antidepressant.

13. The system of claim 8, wherein:
the information relating to the at least one sleep aspect indicates that the patient is not suffering from chronic insomnia.

14. At least one non-transitory computer-readable storage medium storing processor-executable instructions that, when executed by at least one processor, cause the at least one processor to perform a method for treating a patient suffering from at least one mood disorder, the method comprising:
receiving at least one interaction from the patient;
receiving information relating to at least one sleep aspect from the patient and indicating that the patient is not complaining about insomnia; and
treating the at least one mood disorder by outputting, to the patient, information assisting in treatment of the at least one sleep aspect based at least in part on the at least one interaction received from the patient,
wherein the information assisting in the treatment of the at least one sleep aspect comprises at least one element of cognitive behavioral therapy for the at least one sleep aspect.

15. The at least one non-transitory computer-readable storage medium of claim 14, the method further comprising providing training regarding:
sleep hygiene,
sleep restriction,
stimulus control,
sleep scheduling,
cognitive therapy,
relaxation therapy, and/or
mindfulness therapy or training.

16. The at least one non-transitory computer-readable storage medium of claim 14, the method further comprising:
facilitating self-administered cognitive behavioral therapy for the at least one sleep aspect.

17. The at least one non-transitory computer-readable storage medium of claim 16, wherein:
the at least one mood disorder responds to treatment within 3 or fewer weeks of initiation of the treatment.

18. The at least one non-transitory computer-readable storage medium of claim 14, wherein:
the information assisting in the treatment of the at least one sleep aspect comprises:
psychological education material,
relaxation training,
interactive multimedia content for paced breathing, progressive muscle relaxation, imagery-induced relaxation, and/or self-hypnosis,
instructions on patient monitoring of and adjustment of thoughts of the patient,
an interactive sleep diary tracking at least one metric related to sleep behavior of the patient,
instructions on modifying sleep behavior of the patient,
information regarding sleep hygiene and stimulus control,
instructions on sleep restriction and/or sleep windows, and/or
instructions on use of medication.

19. The at least one non-transitory computer-readable storage medium of claim 14, wherein:
the at least one mood disorder comprises at least moderate depression that is treatment-resistant.

20. The at least one non-transitory computer-readable storage medium of claim 14, wherein:
treating the at least one mood disorder comprises treating the at least one mood disorder by outputting, to the patient, the information assisting in treatment of the at least one sleep aspect and by causing administering to the patient an omega-3 fatty acid formulation or an antidepressant.

* * * * *